(12) United States Patent
Xiong et al.

(10) Patent No.: US 12,016,710 B2
(45) Date of Patent: Jun. 25, 2024

(54) METHOD AND APPARATUS BASED ON 3D CAMERA FOR AUTOMATED MEASUREMENT PREPARATION IN MRI SYSTEM

(71) Applicant: Siemens Healthcare GmbH, Erlangen (DE)

(72) Inventors: Jun Xiong, Shenzhen (CN); Kun Zhu, Shenzhen (CN); Fang Yong Sun, Shenzhen (CN); Hui Song, Shenzhen (CN); Xu He, Shenzhen (CN)

(73) Assignee: Siemens Healthineers AG, Erlangen (DE)

( * ) Notice: Subject to any disclaimer, the term of this patent is extended or adjusted under 35 U.S.C. 154(b) by 685 days.

(21) Appl. No.: 17/233,988

(22) Filed: Apr. 19, 2021

(65) Prior Publication Data
US 2021/0330272 A1 Oct. 28, 2021

(30) Foreign Application Priority Data
Apr. 22, 2020 (CN) .......................... 202010320652.9

(51) Int. Cl.
*G06K 9/00* (2022.01)
*A61B 5/00* (2006.01)
(Continued)

(52) U.S. Cl.
CPC .......... *A61B 6/0407* (2013.01); *A61B 5/0033* (2013.01); *A61B 6/0492* (2013.01); *A61B 6/5294* (2013.01)

(58) Field of Classification Search
CPC .. G06K 9/00; A61K 35/12; A61B 6/04; A61B 6/025
(Continued)

(56) References Cited

U.S. PATENT DOCUMENTS 11,272,991 B2 *  3/2022  Ziraknejad .......... G06F 3/04815
2016/0092078 A1  3/2016  Braun et al.
(Continued)

FOREIGN PATENT DOCUMENTS

EP      3520687 A1      8/2019

OTHER PUBLICATIONS

European Search Report dated Sep. 16, 2021, Application No. 21 169 749.5.

*Primary Examiner* — Seyed H Azarian
(74) *Attorney, Agent, or Firm* — Banner & Witcoff Ltd.

(57) ABSTRACT

The disclosure relates to techniques for scan preparation in a medical imaging system. The technique includes triggering a 3D camera acquiring a 2D color and depth image of a patient when a patient bed is at an origin position, inputting the image into a pre-trained first body information model to obtain position information of multiple body feature site points, and calculating position information of multiple candidate scanning regions in the patient bed coordinate system. The technique further includes providing the position information of the multiple candidate scanning regions to a medical imaging application apparatus, so that the medical imaging application apparatus determines position information of a current scanning region in the patient bed coordinate system and controls the patient bed to move the current scanning region to a scanning center of a medical imaging device according to the position of the patient bed relative to the scanning center.

16 Claims, 6 Drawing Sheets

(51) Int. Cl.
*A61B 6/00* (2006.01)
*A61B 6/04* (2006.01)
*A61K 35/12* (2015.01)

(58) Field of Classification Search
USPC ........ 382/100, 103, 106–107, 128–133, 154,
382/162, 168, 173, 181, 189, 199, 224,
382/254, 274–276, 286–291, 312; 378/4,
378/21, 28
See application file for complete search history.

(56) References Cited

U.S. PATENT DOCUMENTS

| | | |
|---|---|---|
| 2017/0100089 A1 | 4/2017 | Chang et al. |
| 2017/0165501 A1* | 6/2017 | Rapaka ..................... G06T 7/73 |
| 2017/0249423 A1* | 8/2017 | Wang ................. G06V 10/7557 |
| 2017/0311841 A1 | 11/2017 | Rothgang |
| 2017/0316562 A1 | 11/2017 | Haberland et al. |
| 2017/0354385 A1* | 12/2017 | Lerch ................... A61B 6/4435 |
| 2018/0116518 A1 | 5/2018 | Rinck et al. |
| 2018/0140270 A1 | 5/2018 | Profio et al. |
| 2018/0247427 A1* | 8/2018 | Geiger ................... G06V 20/64 |
| 2021/0146158 A1* | 5/2021 | Wirtz ................. G01R 33/5673 |

* cited by examiner

METHOD AND APPARATUS BASED ON 3D CAMERA FOR AUTOMATED MEASUREMENT PREPARATION IN MRI SYSTEM

CROSS-REFERENCE TO RELATED APPLICATIONS

The present application claims the benefit of the filing date of China patent application no. CN 202010320652.9, filed on Apr. 22, 2020, the contents of which are incorporated herein by reference in their entirety.

TECHNICAL FIELD

The disclosure relates to the medical field and, in particular, to techniques for scan preparation based on a 3D camera in a medical imaging system.

BACKGROUND

In a medical imaging system such as a magnetic resonance (MR) imaging system or computed tomography (CT) imaging system, some preparation needs to be done before beginning the formal scan.

For example, taking an MR system as an example, preparation for scanning may include the following steps: 1) a patient lies on a patient bed; 2) patient positioning is performed including determining the position of a target scanning region to be scanned in the patient, then moving this to the scanning center, e.g. magnet center, of the medical imaging system. 3) The patient is registered, i.e. patient information is inputted in an application software system operating interface of the MR system; the patient information includes full name, ID, height, weight, and patient posture information, etc. 4) Scan parameters such as a corresponding protocol set are selected and scanning is begun. Of course, in other instances, steps 3) and 4) above may also be performed before steps 1) and 2).

SUMMARY

In view of the above, embodiments of the present disclosure propose a method for scan preparation in a medical imaging system and a system for scan preparation in a medical imaging system, for the purpose of increasing the degree of automation of scan preparation.

A method for scan preparation in a medical imaging system that is proposed in an embodiment of the present disclosure comprises: triggering a 3D camera mounted above a patient bed in the medical imaging system to acquire a 2D color and depth image of a patient at the present time, when the patient bed is at a predetermined position (e.g. an origin position or approximate origin position, the origin being a default or initial position of the patient bed for instance); receiving the 2D color and depth image acquired by the 3D camera, and inputting the 2D color and depth image into a pre-trained first body information model, to obtain position information, outputted by the first body information model, of multiple body feature site points in a camera coordinate system or patient bed coordinate system; the first body information model being obtained by training, using multiple sets of 2D color and depth images acquired in advance (e.g. predetermined) as an input parameter set, and using position information of multiple body feature site points in the camera coordinate system or patient bed coordinate system, corresponding to each set of 2D color and depth images and acquired in advance (e.g. predetermined), as an output parameter set; wherein, when the position information is position information in the camera coordinate system, the position information of the multiple body feature site points in the camera coordinate system is converted into position information in the patient bed coordinate system, according to a conversion relationship between the patient bed coordinate system and the camera coordinate system that is determined when the camera is calibrated; calculating position information of multiple candidate scanning regions in the patient bed coordinate system, according to the position information of the multiple body feature site points in the patient bed coordinate system; providing the position information of the multiple candidate scanning regions in the patient bed coordinate system to a medical imaging application apparatus, so that the medical imaging application apparatus determines position information of a current scanning region in the patient bed coordinate system, and controls the patient bed to move the current scanning region to a scanning center of a medical imaging device according to the position information of the current scanning region in the patient bed coordinate system and the position of the patient bed relative to the scanning center.

In one embodiment, when a coil covers a body region of the patient, information of the body region covered by the coil that is outputted by the first body information model is further obtained; and the method further comprises:
  providing the information of the body region covered by the coil to the medical imaging application apparatus so that the medical imaging application apparatus determines a candidate scanning region supported by the medical imaging system according to the information of the body region covered by the coil, and then selects a current scanning region from the candidate scanning region supported by the medical imaging system.

One embodiment further comprises: inputting the 2D color and depth image into a pre-trained second body information model to obtain height, weight, and posture information of the patient that is outputted by the second body information model; the second body information model being obtained by training, using multiple sets of 2D color and depth images acquired in advance as an input parameter set, and using height, weight, and posture information, corresponding to each set of 2D color and depth images and acquired in advance, as an output parameter set; and providing the height, weight, and posture information of the patient to the medical imaging application apparatus, so that the medical imaging application apparatus uses the height, weight, and posture information to perform information registration for the patient.

In one embodiment, the step of the medical imaging application apparatus using the height, weight, and posture information to perform information registration for the patient comprises: in a patient registration stage, the medical imaging application apparatus pre-filling a corresponding information box with the height, weight, and posture information for presentation to a user.

In one embodiment, the step of the medical imaging application apparatus using the height, weight, and posture information to perform information registration for the patient comprises: upon receiving a scan initiation instruction triggered by a user, the medical imaging application apparatus comparing the height, weight, and posture information with height, weight, and posture information registered in advance by the user, and when deviation information of the height and weight exceeds a set threshold or the posture information is not consistent (e.g. exceeds a predetermined difference threshold or error), popping up (e.g. displaying) a warning message box, and determining height, weight, and posture information to be used in the current scan according to a user selection.

An acquisition control and image analysis apparatus proposed in an embodiment of the present disclosure comprises: an acquisition control module configured to trigger a 3D camera mounted above a patient bed in a medical imaging system to acquire a 2D color and depth image of a patient at the present time, when the patient bed is at a predetermined position (e.g. an origin position or approximate origin position); and an image analysis module configured to: receive the 2D color and depth image acquired by the 3D camera and input the 2D color and depth image into a pre-trained first body information model, to obtain position information, outputted by the first body information model, of multiple body feature site points in a camera coordinate system or patient bed coordinate system; when the position information is position information in the camera coordinate system, further convert the position information of the multiple body feature site points in the camera coordinate system into position information in the patient bed coordinate system, according to a conversion relationship between the patient bed coordinate system and the camera coordinate system that is determined when the camera is calibrated; calculate position information of multiple candidate scanning regions in the patient bed coordinate system, according to the position information of the multiple body feature site points in the patient bed coordinate system; and provide the position information of the multiple candidate scanning regions in the patient bed coordinate system to a medical imaging application apparatus so that the medical imaging application apparatus determines position information of a current scanning region in the patient bed coordinate system, and moves the current scanning region to a scanning center of a medical imaging device according to the position information of the current scanning region in the patient bed coordinate system and the position of the patient bed relative to the scanning center; wherein the first body information model is obtained by training, using multiple sets of 2D color and depth images acquired in advance as an input parameter set, and using position information of multiple body feature site points in the camera coordinate system or patient bed coordinate system, corresponding to each set of 2D color and depth images and acquired in advance, as an output parameter set.

In one embodiment, when a coil covers a body region of the patient, the image analysis module further obtains information of the body region covered by the coil that is outputted by the first body information model, and further provides the information of the body region covered by the coil to the medical imaging application apparatus, so that the medical imaging application apparatus determines a candidate scanning region supported by the medical imaging system according to the information of the body region covered by the coil, and then selects a current scanning region from the candidate scanning region supported by the medical imaging system.

In one embodiment, the image analysis module further inputs the 2D color and depth image into a pre-trained second body information model, to obtain height, weight, and posture information of the patient that is outputted by the second body information model; and provides the height, weight, and posture information of the patient to the medical imaging application apparatus so that the medical imaging application apparatus uses the height, weight, and posture information to perform information registration for the patient; wherein the second body information model is obtained by training, using multiple sets of 2D color and depth images acquired in advance as an input parameter set, and using height, weight, and posture information, corresponding to each set of 2D color and depth images and acquired in advance, as an output parameter set.

An image acquisition and analysis system proposed in an embodiment of the present disclosure comprises: at least one memory and at least one processor, wherein: the at least one memory is configured to store a computer program; and the at least one processor is configured to call the computer program stored in the at least one memory to perform the method for scan preparation in a medical imaging system as described in any one of the above embodiments.

An image acquisition and analysis system proposed in an embodiment of the present disclosure comprises: a 3D camera mounted at a set position above a medical imaging system; and the acquisition control and image analysis apparatus as described in any one of the above embodiments.

A system for scan preparation in a medical imaging system that is proposed in an embodiment of the present disclosure comprises: an image acquisition and analysis system as described above; and a medical imaging application apparatus configured to determine position information of a current scanning region in a patient bed coordinate system according to position information of multiple candidate scanning regions in the patient bed coordinate system that is provided by the image acquisition and analysis system, and control the patient bed to move the current scanning region to a scanning center of a medical imaging device according to the position information of the current scanning region in the patient bed coordinate system and the position of the patient bed relative to the scanning center.

In one embodiment, the medical imaging application apparatus is further configured to perform information registration for the patient according to height, weight, and posture information of the patient that is provided by the image acquisition and analysis system.

Another system for scan preparation in a medical imaging system that is proposed in an embodiment of the present disclosure comprises: a first apparatus and a second apparatus; wherein the first apparatus comprises a first memory and a first processor, wherein: the first memory is configured to store a computer program; the first processor is configured to call the computer program stored in the first memory, to perform the operation of: triggering a 3D camera mounted above a patient bed in the medical imaging system to acquire a 2D color and depth image of a patient at the present time, when the patient bed is at a predetermined position (e.g. an origin position or approximate origin position); the second apparatus comprises a second memory and a second processor, wherein: the second memory is configured to store a computer program; the second processor is configured to call the computer program stored in the second memory to perform the following operations: receiving the 2D color and depth image acquired by the 3D camera, and inputting the 2D color and depth image into a pre-trained first body information model, to obtain position information, outputted by the first body information model, of multiple body feature site points in a camera coordinate system or patient bed coordinate system; the first body information model being obtained by training, using multiple sets of 2D color and depth images acquired in advance as an input parameter set, and using position information of multiple body feature site points in the camera coordinate system or patient bed coordinate system, corresponding to each set of 2D color and depth images and acquired in advance, as an output parameter set; wherein, when the position information is position information in the camera coordinate system, the position information of the multiple body feature site points in the camera coordinate system is converted into position information in the patient bed coordinate system, according to a conversion relationship between the patient bed coordinate system and the camera coordinate system that is determined when the camera is calibrated; calculating position information of multiple candidate scanning regions in the patient bed coordinate system, according to the position information of the multiple body feature site points in the patient bed coordinate system; obtaining determined position information of a current scanning region in the patient bed coordinate system according to the position information of the multiple candidate scanning regions in the patient bed coordinate system, and controlling the patient bed to move the current scanning region to a scanning center of a medical imaging device according to the position information of the current scanning region in the patient bed coordinate system and the position of the patient bed relative to the scanning center.

A computer readable storage medium proposed in an embodiment of the present disclosure has stored thereon a computer program; the computer program can be executed by a processor to realize the method for scan preparation in a medical imaging system as described in any one of the above embodiments.

As can be seen from the solution above, in embodiments of the present disclosure, the 3D camera is used to acquire a 2D color and depth image of the patient at a present time, and the image acquired by the 3D camera is inputted into a pre-trained first body information model, and it is then possible to obtain position information, outputted by the first body information model, of body feature site points in the camera coordinate system or patient bed coordinate system, then position information of multiple candidate scanning regions in the patient bed coordinate system is calculated, this information is provided to the medical imaging application apparatus of the medical imaging system, the medical imaging application apparatus determines therefrom position information of a selected current scanning region in the patient bed coordinate system, and controls the patient bed to move the current scanning region to the scanning center of the medical imaging device according to the position information of the current scanning region in the patient bed coordinate system and the position of the patient bed relative to the scanning center, thereby increasing the degree of automation of patient positioning in the scan preparation process.

In addition, the image acquired by the 3D camera is further inputted into a pre-trained second body information model, and height, weight, and posture information of the patient that is outputted by the second body information model is obtained; the height, weight, and posture information of the patient is provided to the medical imaging application apparatus, so that the medical imaging application apparatus uses the height, weight, and posture information to perform information registration for the patient, thereby increasing the degree of automation of patient registration in the scan preparation process.

Furthermore, the first body information model is trained to further output information of a body region covered by a coil, and the information of the body region covered by the coil is provided to the medical imaging application apparatus so that the medical imaging application apparatus uses the information of the body region covered by the coil to determine or reduce the scope of scanning regions currently supported by the medical imaging system.

BRIEF DESCRIPTION OF THE DRAWINGS/FIGURES

Preferred embodiments of the present disclosure are described in detail below with reference to the accompanying drawings, to give those skilled in the art a clearer understanding of the abovementioned and other features and advantages of the present disclosure.

KEY TO THE DRAWINGS

| Label | Meaning |
| --- | --- |
| 110 | image acquisition and analysis system |
| 111 | 3D camera |
| 112 | dedicated computer |
| 120 | medical imaging system |
| 121 | medical imaging device |
| 1211 | touch screen or control panel |
| 122 | patient bed |
| 130 | mounting system |
| 140 | ceiling |
| 150 | patient |
| S21-S24, S31-S38, S41-S51 | steps |
| 500, 600 | acquisition control and image analysis apparatus |
| 501 | acquisition control module |
| 502 | image analysis module |
| 601 | memory |
| 602 | processor |
| 603 | bus |
| 700 | image acquisition and analysis system |
| 800 | system for scan preparation in medical imaging system |
| 801 | medical imaging application apparatus |
| 910 | first apparatus |
| 911 | first memory |
| 912 | first processor |
| 913 | first communication port |

-continued

| Label | Meaning |
|---|---|
| 914 | first bus |
| 920 | second apparatus |
| 921 | second memory |
| 922 | second processor |
| 923 | second communication port |
| 924 | second bus |

DETAILED DESCRIPTION

In embodiments of the present disclosure, account is taken of the fact that for the patient positioning step in the majority of common applications, the operator typically manually performs the following steps: a) moving the target scanning region of the patient quickly and roughly into the magnet aperture by means of a control panel or apparatus; b) switching on a laser marker, which will show on the patient's body; c) slowly moving the diagnostic bed and determining the precise position of the target scanning region of the patient, as indicated by the laser marker; and d) moving the target scanning region of the patient to the scanning center, e.g. magnet center, by means of the control panel or apparatus. As can be seen, the manual positioning process described above is complex and time-consuming, and the accuracy of patient positioning is dependent on the operator's knowledge and experience of human anatomy, so results are neither standardized nor reproducible.

Thus, in embodiments of the present disclosure, it is the intention to provide a scheme for patient positioning based on a three-dimensional (3D) camera in a medical imaging system. The precise position of the target scanning region of the patient that is used for positioning is obtained with the aid of pictures acquired by the 3D camera and first body information obtained (e.g. by training) in advance.

In addition, account is taken of the fact that for the patient registration step in the majority of common applications, patient height and weight information can be measured by means of a height ruler and a set of scales and/or a weighing instrument. These measurements require a certain amount of time, and the measured values need to be filled in manually. However, in certain emergencies, it is not really possible to measure, for example, a patient lying on a patient bed or unable to move, such as a stroke patient or comatose patient. Thus, in some situations, for convenience or to save time, patient data comes from estimations made by the operator or by the patient himself, but the estimated data is generally not accurate enough; this will have a direct effect on scanning, e.g. the calculation of SAR (Specific Absorption Rate). Patient posture information includes head-first/feet-first entry, lying face down, lying face up or lying on one side, etc.; the operator observes the patient's posture and fills it in manually. Sometimes, the operator might inadvertently input an incorrect patient posture, resulting in incorrect directional information in the medical image; this might cause a mistaken diagnosis in which case the consequences will be very serious.

Thus, in embodiments of the present disclosure, it is the intention to provide a scheme for patient registration based on a 3D camera in a medical imaging system. The height, weight, and posture information used for registration is obtained with the aid of pictures acquired by 3D photography and a second body information model obtained by training in advance.

In order to clarify the object, technical solution, and advantages of the present disclosure, the present disclosure is explained in further detail below by way of exemplary embodiments. The solution of the present disclosure is expounded below by describing a number of representative embodiments to make the description concise and intuitive. The large number of details in the embodiments are intended to assist with understanding of the solution of the present disclosure. However, obviously the technical solution of the present disclosure need not be limited to these details or specific examples when implemented. To avoid making the solution of the present disclosure unnecessarily confusing, some embodiments are not described meticulously but merely outlined. As used herein, "comprises" means "including but not limited to," while "according to . . . " means "at least according to . . . , but not limited to only according to . . . " In cases in which the quantity of a component is not specified herein, there may be one or more of the component, additional components, fewer components, alternative components, etc.; this may also be interpreted as meaning at least one.

Figure 1:
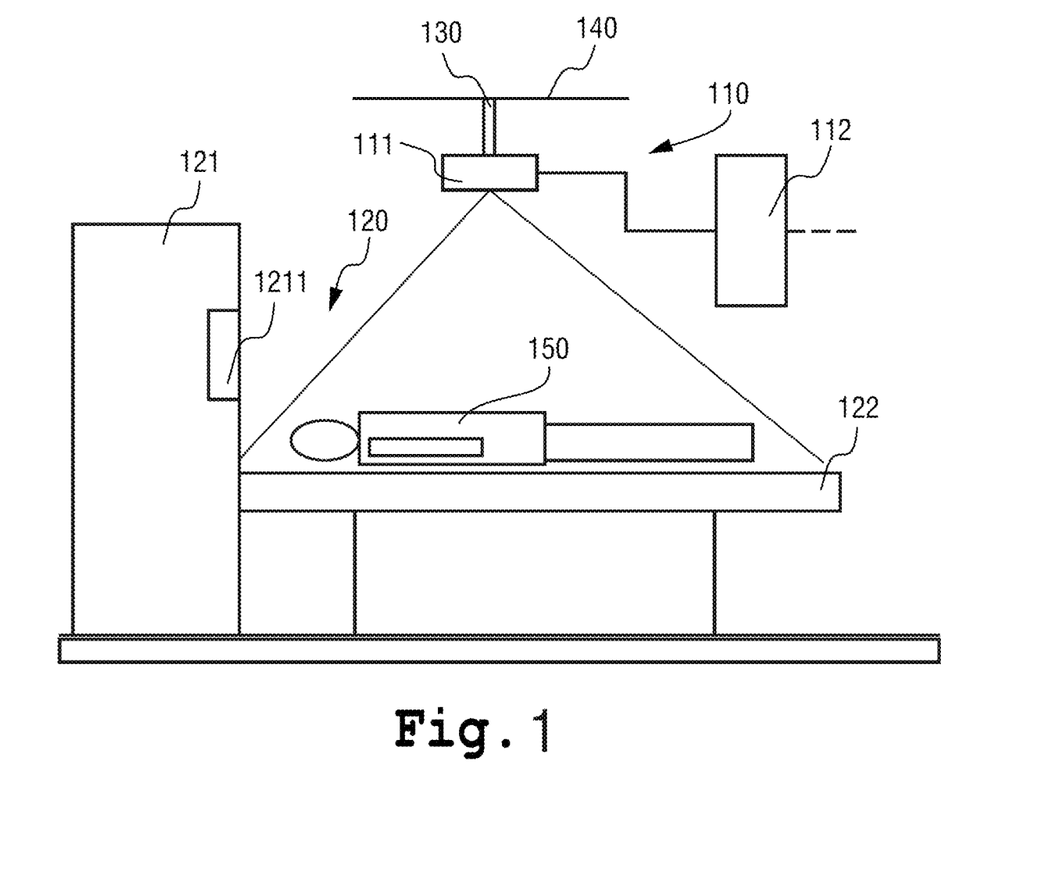
FIG. 1 is a structural schematic diagram of an example implementation environment in various embodiments of the present disclosure.

FIG. 1 is an example structural schematic diagram of an implementation environment in various embodiments of the present disclosure. As shown in FIG. 1, the implementation environment comprises an image acquisition and analysis system 110 and a medical imaging system 120. The image acquisition and analysis system 110 comprises a 3D camera 111 and an acquisition control and image analysis apparatus (not shown in FIG. 1). The medical imaging system 120 comprises a medical imaging device 121, a patient bed (or patient operating table) 122, and a medical imaging application apparatus (not shown in FIG. 1). The acquisition control and image analysis apparatus may be implemented in a computer of the medical imaging application apparatus, or as a separate computer, such as a dedicated computer 112. When the acquisition control and image analysis apparatus is implemented as a separate computer, communication with the medical imaging application apparatus may be conducted via any suitable network.

The 3D camera 111 is configured to continuously capture two-dimensional (2D) color (RGB) and depth images of the patient lying on the patient bed. When the 3D camera 111 is mounted at a suitable height on a ceiling (or support) 140 by means of a mounting system 130, the visual field can cover all or most of the patient bed 122, and a full picture of the patient 150 can be obtained in a single action.

The acquisition control and image analysis apparatus may comprise an acquisition control module and an image analysis module. The acquisition control module may be configured to trigger image acquisition by the 3D camera 111. The image analysis module is configured to analyze the images acquired by the 3D camera and to provide a corresponding result to the medical imaging application apparatus.

By way of example and not limitation, the medical imaging device 121 may be a magnetic resonance imaging (MRI) device or a computed tomography (CT) machine, and in any case be configured to perform an imaging scan of the target scanning region of a patient placed at the scanning center on the basis of determined scanning parameters. A touch screen or control panel 1211 may be provided at the medical imaging device 121. The patient bed 122 is configured to carry the patient and to move the target scanning region of the patient to the scanning center of the medical scanning device 121. The medical imaging application apparatus is configured to perform patient positioning and patient registration according to an image analysis result provided by an image analysis system.

Figure 2:
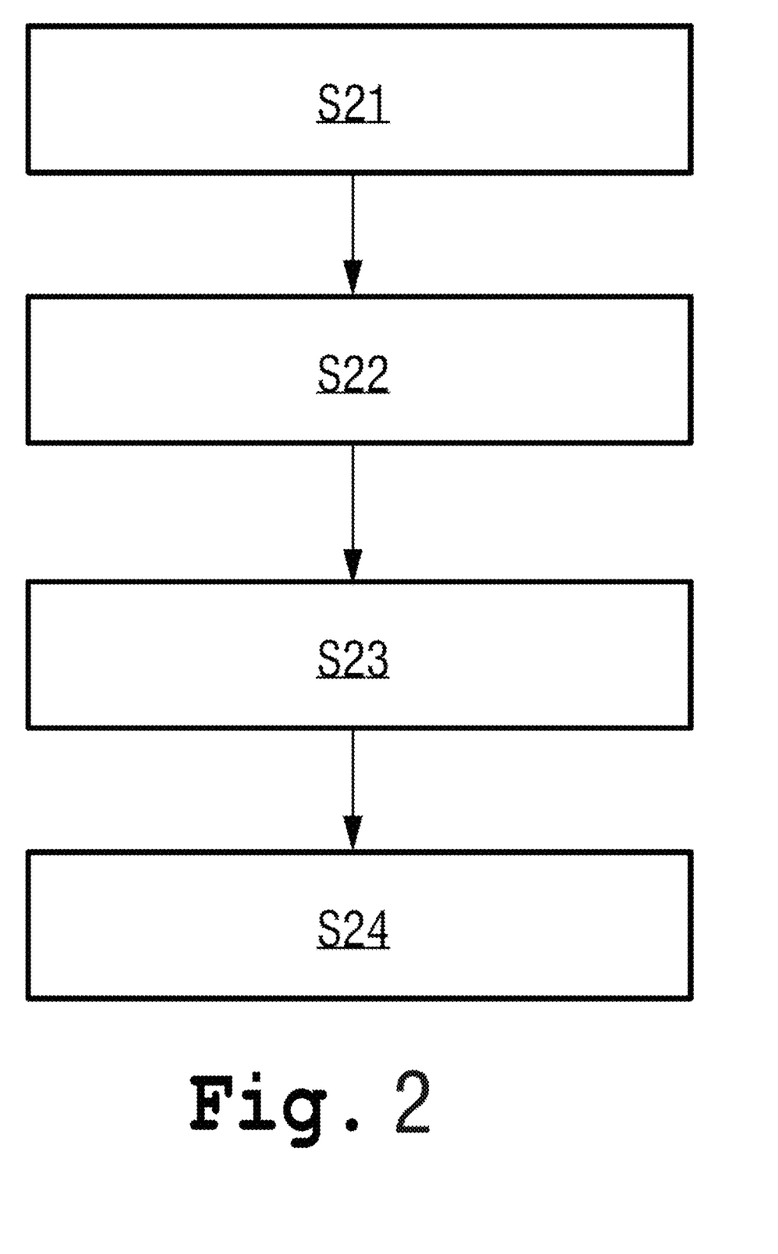
FIG. 2 is an example flow chart of a method based on a 3D camera for acquiring body information to perform scan preparation in a medical imaging system in an embodiment of the present disclosure.

FIG. 2 is an example flow chart of a method based on a 3D camera for acquiring body information to perform scan preparation in a medical imaging system in an embodiment of the present disclosure. The method is realized mainly by the acquisition control and image analysis apparatus in the 3D image acquisition and analysis system 110. As FIG. 2 shows, the method may comprise the following steps:

Step S21: when the patient bed moves to a predetermined position (e.g. an origin position or approximate origin position), the 3D camera 111 is triggered to acquire a 2D color and depth image of the patient. In this embodiment, the medical imaging application apparatus can ascertain the state and position of the bed, and therefore instruct or otherwise command the acquisition control module in the acquisition control and image analysis apparatus to trigger the acquisition of the 2D color and depth image of the patient by the 3D camera when the patient bed moves to the a predetermined position (e.g. an origin position or approximate origin position), and transfer the acquired image to the image analysis module to begin image analysis. When the patient bed leaves the origin position or approximate origin position, the medical imaging application apparatus can instruct or otherwise command the acquisition control and image analysis apparatus to stop image acquisition and analysis.

In general, when the patient bed moves to the origin position or approximate origin position (e.g. within a specified threshold tolerance of the origin position such as 1%, 5%, 10%, etc.), it is possible to ensure that the patient can be located completely within the visual field of the 3D camera; thus, in this step, the image acquisition by the 3D camera can be triggered when the patient bed is moved to the predetermined position.

Step S22: the 2D color and depth image is inputted into a pre-trained first body information model to obtain position information, which is outputted by the first body information model, of multiple body feature site points in a camera coordinate system or a patient bed coordinate system. The body feature site points comprise anatomical sites that are easily identified in the image, such as the top of the head, tip of the nose, chin, eyes, ears, wrist joint, elbow joint, knee joint, ankle joint, etc. In this embodiment, 37 feature site points can be identified in this manner by way of example and not limitation, although any suitable number of body feature site points may be identified. In this step, the first body information model may be obtained by training, using multiple sets of 2D color and depth images acquired in advance as an input parameter set, and using position information of multiple body feature site points in the camera coordinate system or patient bed coordinate system, corresponding to each set of 2D color and depth images and acquired in advance, as an output parameter set.

When the position information is position information in the camera coordinate system, in this embodiment it is further possible to convert the position information of the multiple body feature site points in the camera coordinate system into position information in the patient bed coordinate system, according to a conversion relationship between the patient bed coordinate system and the camera coordinate system that is determined when the camera is calibrated.

In addition, in this step, the 2D color and depth image may also be inputted into a pre-trained second body information model, to obtain height, weight, and posture information of the patient that is outputted by the second body information model. The second body information model may be obtained by training using multiple sets of 2D color and depth images acquired in advance as an input parameter set, and using height, weight, and posture information, corresponding to each set of 2D color and depth images and acquired in advance, as an output parameter set.

In a particular implementation, the first body information model and second body information model may be two separate models or the same model. When they are the same model, the output parameter set comprises position information of multiple body feature site points in the camera coordinate system or patient bed coordinate system, and body height, weight, and posture information, corresponding to each set of 2D color and depth images and acquired in advance.

Step S23: position information of multiple candidate scanning regions in the patient bed coordinate system is calculated according to the position information of the multiple body feature site points in the patient bed coordinate system. In this step, since body feature site points and center points of corresponding candidate scanning regions satisfy certain anatomical proportional relationships, after each feature site point has been determined the center point of a candidate scanning region can be calculated at the same time according to body depth (thickness) information in the depth image. At the same time, three-dimensional ranges of different candidate scanning regions of different patients can be calculated according to positions of body feature points and anatomical proportional relationships, and all candidate scanning regions can thus be determined.

Step S24: the position and range information of the multiple candidate scanning regions in the patient bed coordinate system is provided to the medical imaging application apparatus; in the case where patient height, weight, and posture information was also obtained at the same time in step S22, the height, weight, and posture information of the patient may further be provided to the medical imaging application apparatus in this step. After receiving the position information of multiple candidate scanning regions in the patient bed coordinate system, the medical imaging application apparatus can determine position information of a current scanning region in the patient bed coordinate system, and move the current scanning region to the scanning center according to the position information of the current scanning region in the patient bed coordinate system and the position of the patient bed relative to the scanning center.

After receiving the height, weight, and posture information, the medical imaging application apparatus can use the height, weight, and posture information to perform information registration for the patient.

Steps S22-S24 above may be implemented by the image analysis module in the acquisition control and image analysis apparatus. Steps S21-S24 above may be repeated at a fixed frame rate to continuously monitor the patient. In this way, relevant information in the medical imaging application apparatus may be updated in real time.

In addition, when a coil covers a body region of the patient, in step S22 the first body information model may further obtain and output information of the body region covered by the coil. Correspondingly, an input parameter set needed to train the first body information model comprises a 2D color and depth image when a coil covers a body region of the patient, and an output parameter set further comprises information of the body region covered by the coil. Then in step S24, the information of the body region covered by the coil may be further provided to the medical imaging application apparatus so that the medical imaging application apparatus determines candidate scanning regions currently supported by the system according to the body region covered by the coil.

The entire scan preparation method using the method of FIG. 2 is described in detail below, taking an MRI system by way of example and not limitation.

Figure 3:
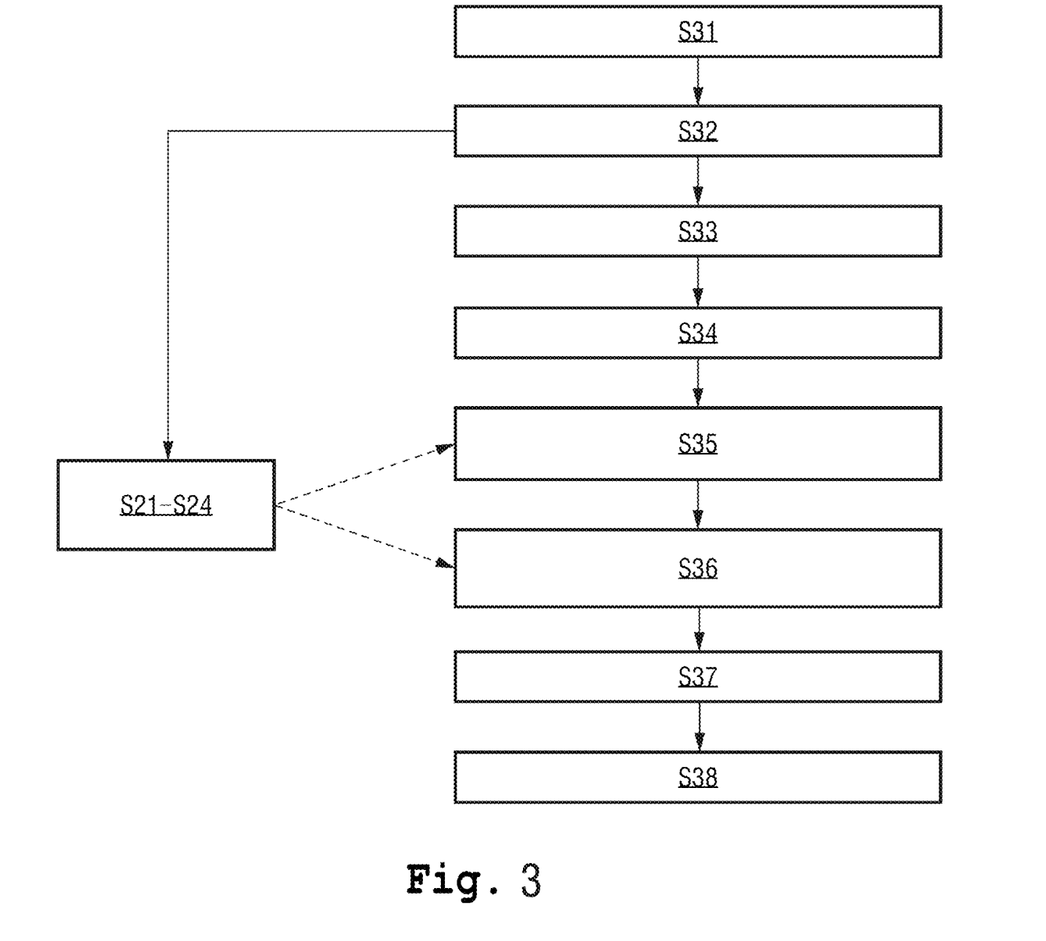
FIG. 3 is an example flow chart of a method for scan preparation in a medical imaging system in an embodiment of the present disclosure.

FIG. 3 is an example flow chart of a method for scan preparation in a medical imaging system in an embodiment of the present disclosure. This example is based on a scenario in which patient registration is performed after patient positioning. As FIG. 3 shows, the method may comprise the following steps:

Step S31: the patient is placed on the patient bed.

Step S32: the patient bed is moved to the predetermined position (e.g. an origin position or approximate origin position), and the medical imaging application apparatus triggers the acquisition control and image analysis apparatus to perform steps S21-S24.

Step S33: the medical imaging application apparatus presents candidate scanning regions supported by the medical imaging system. In this step, the candidate scanning regions supported by the medical imaging system and basic information such as the full name of the patient may be displayed on a display screen or the touch screen of the magnet, or may also be displayed on a computer display screen outside a scanning room. The candidate scanning regions supported by the medical imaging system may be determined according to candidate scanning regions supported by the 3D image acquisition and analysis system 110 and/or a scanning region supported by the coil that is determined in advance.

In addition, in this embodiment, when the coil covers a body region of the patient, the body region covered by the coil is further obtained according to the 2D color and depth image of the patient acquired in real time by the 3D camera, then in Step S33, the candidate scanning regions supported by the system may further be determined or reduced in scope according to the body region covered by the coil that is identified on the basis of a 3D image. That is, the candidate scanning regions supported by the medical imaging system may be determined according to any one of, or any combination of, the following: the candidate scanning regions supported by the 3D image acquisition and analysis system 110, the scanning region supported by the coil that is determined in advance, and the body region covered by the coil that is identified on the basis of the 3D image. If it is determined according to at least two of the candidate scanning regions supported by the 3D image acquisition and analysis system 110, the scanning region supported by the coil that is determined in advance, and the body region covered by the coil that is identified on the basis of the 3D image, then the intersection of the at least two can be taken.

Step S34: the medical imaging application apparatus determines a current scanning region from the candidate scanning regions according to a user selection and filters a protocol set or workflow according to the current scanning region.

Step S35: after the user has triggered an operation to move the scanning region to the magnet center, the medical imaging application apparatus moves the current scanning region to the magnet center according to the position information of the current scanning region in the patient bed coordinate system that is provided by the acquisition control and image analysis apparatus and the position of the patient bed relative to the scanning center.

Step S36: when the user leaves the scanning room, enters the control room to begin patient registration, and opens a patient registration dialog box interface, the medical imaging application apparatus pre-fills a corresponding information box in the patient registration dialog box interface according to the height, weight, and posture information of the patient that is provided by the acquisition control and image analysis apparatus, for presentation to the user.

Step S37: the medical imaging application apparatus determines a current protocol set or workflow from the protocol set or workflow filtered out in step S34, according to a user selection. Scan preparation ends here, and scanning can subsequently be begun.

Step S38: scanning is begun according to a user trigger.

Figure 4:
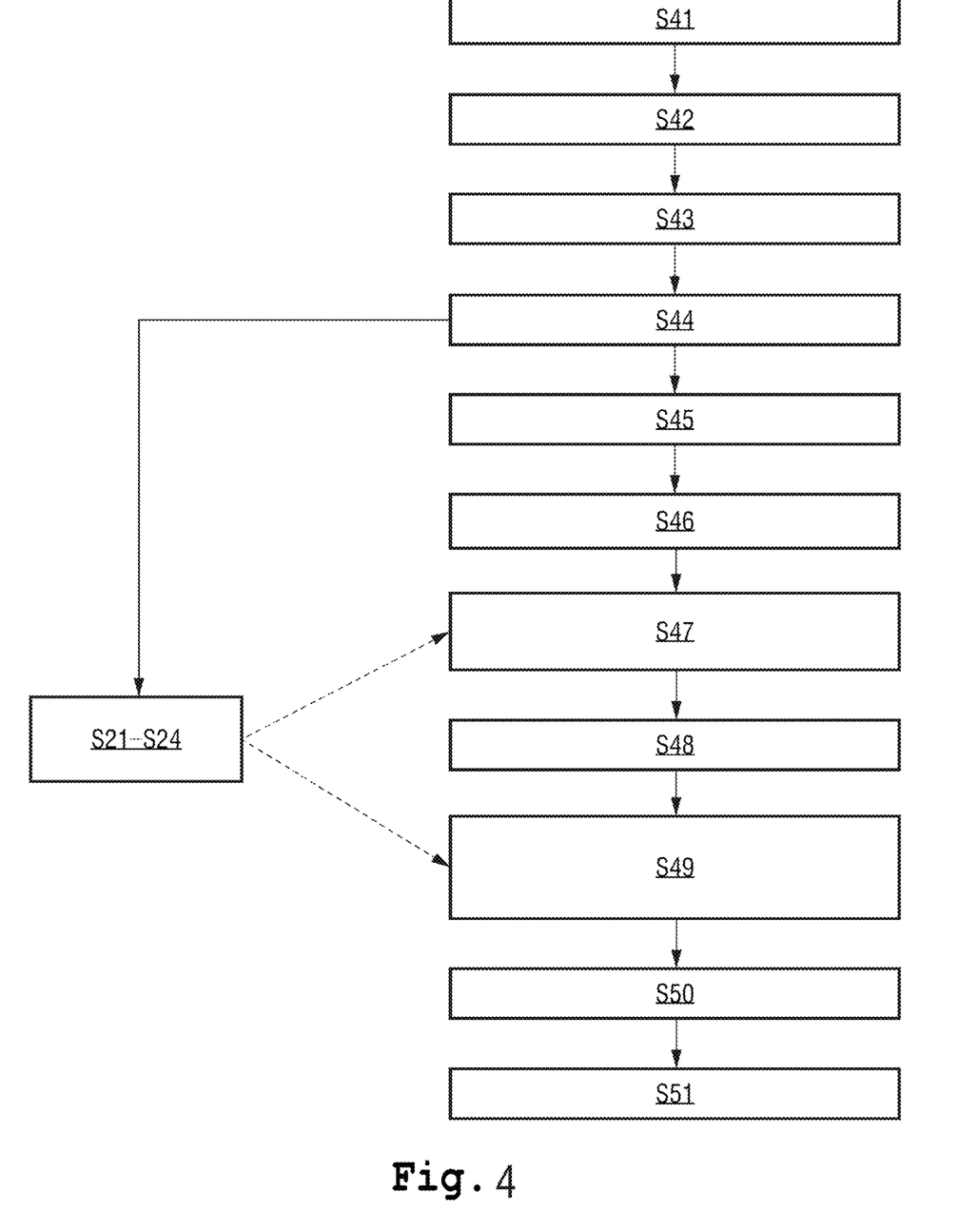
FIG. 4 is an example flow chart of a method for scan preparation in a medical imaging system in an embodiment of the present disclosure.

FIG. 4 is an example flow chart of a method for scan preparation in a medical imaging system in another embodiment of the present disclosure. This example is based on a scenario in which patient registration is performed before patient positioning. As FIG. 4 shows, the method may comprise the following steps:

In this example, patient registration is begun only after the patient has been positioned and sent into the scanning center; at this time, the 3D image acquisition and analysis system integrated in the medical imaging system operates according to the following steps:

Step S41: the medical imaging application apparatus receives patient information registered by the user; the patient information comprises patient height, weight, and posture information.

Step S42: the medical imaging application apparatus determines the current protocol set or workflow. In this step, the current protocol set may be determined according to a user selection, or the protocol set used in the previous scan may be determined as the current protocol set of the present scan.

Step S43: after the user has left the control room and come to the scanning room, the patient is placed on the patient bed.

Steps S44-S45 are the same as steps S32 and S33 above.

Step S46: the medical imaging application apparatus determines the current scanning region from the candidate scanning regions according to the patient information registered in step S41.

Step S47 is the same as step S35 above.

Step S48: after the user has arrived in the operating room, a scan initiation instruction triggered by the user is received.

Step S49: the medical imaging application apparatus compares the height, weight, and posture information of the patient that is provided by the acquisition control and image analysis apparatus with the height, weight, and posture information registered in step S41; when deviation information of the height and weight exceeds a set threshold or the posture information is not consistent (e.g. exceeds a predetermined difference threshold or error), a warning message box can pop up to display the deviation prominently, and step S50 is performed. Otherwise, step S51 is performed, and no message need be displayed.

Step S50: height, weight, and posture information to be used in the current scan is determined according to a user selection.

Step S51: scanning is begun.

As can be seen, in this embodiment, after the user has clicked on "start scan" in step S48, step S49 will be triggered to perform a patient information check; the actual scan in step S51 will only begin once the check has passed.

The method for scan preparation in a medical imaging system in embodiments of the present disclosure has been described in detail above; the system for scan preparation in a medical imaging system in embodiments of the present disclosure is described in detail below. The system for scan preparation in a medical imaging system in embodiments of the present disclosure can be used to implement the method for scan preparation in a medical imaging system in embodiments of the present disclosure. For particulars not disclosed in detail in system embodiments of the present disclosure, reference can be made to the corresponding description in method embodiments of the present disclosure; an item-by-item description is not repeated here.

Figure 5:
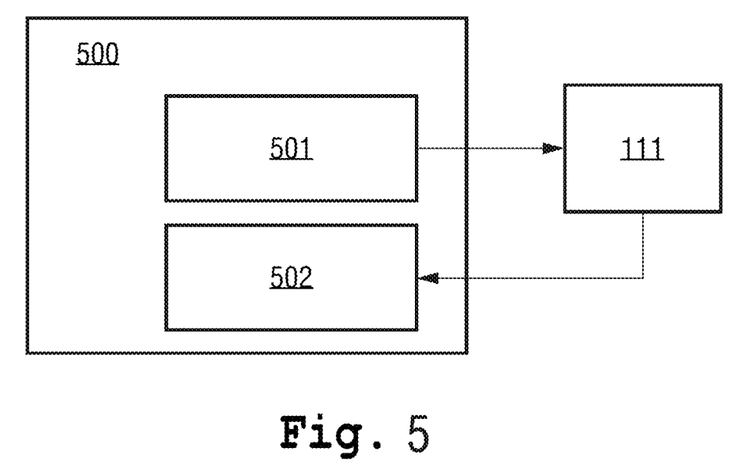
FIG. 5 is an example structural diagram of the acquisition control and image analysis apparatus in an embodiment of the present disclosure.

FIG. 5 is an example structural diagram of the acquisition control and image analysis apparatus in an embodiment of the present disclosure. As shown in FIG. 5, the apparatus 500 may comprise an acquisition control module 501 and an image analysis module 502.

The acquisition control module 501 is configured to trigger the 3D camera 111 mounted above the patient bed to acquire a 2D color and depth image of the patient at the present time, when the patient bed in the medical imaging system is at a predetermined position (e.g. an origin position or approximate origin position).

The image analysis module 502 is configured to receive the 2D color and depth image acquired by the 3D camera 111 and input the 2D color and depth image into a pre-trained first body information model, to obtain position information, outputted by the first body information model, of multiple body feature site points in a camera coordinate system or patient bed coordinate system; when the position information is position information in the camera coordinate system, to further convert the position information of the multiple body feature site points in the camera coordinate system into position information in the patient bed coordinate system, according to a conversion relationship between the patient bed coordinate system and the camera coordinate system that is determined when the camera is calibrated; to calculate position information of multiple candidate scanning regions in the patient bed coordinate system, according to the position information of the multiple body feature site points in the patient bed coordinate system; and to provide the position information of the multiple candidate scanning regions in the patient bed coordinate system to the medical imaging application apparatus, so that the medical imaging application apparatus determines position information of a current scanning region in the patient bed coordinate system, and moves the current scanning region to the scanning center of the medical imaging device according to the position information of the current scanning region in the patient bed coordinate system and the position of the patient bed relative to the scanning center.

The first body information model is obtained by training, using multiple sets of 2D color and depth images acquired in advance as an input parameter set, and using position information of multiple body feature site points in the camera coordinate system or patient bed coordinate system, corresponding to each set of 2D color and depth images and acquired in advance, as an output parameter set.

In another embodiment, when a coil covers a body region of the patient, the image analysis module 502 may further obtain information of the body region covered by the coil that is outputted by the first body information model, and further provide the information of the body region covered by the coil to the medical imaging application apparatus in the medical imaging system so that so that the medical imaging application apparatus presents candidate scanning regions supported by the medical imaging system; wherein the candidate scanning regions supported by the medical imaging system are determined according to any one of, or any combination of: candidate scanning regions supported by the 3D image acquisition and analysis system, a scanning region supported by the coil that is determined in advance, and the body region covered by the coil.

In another embodiment, the image analysis module 502 may further input the 2D color and depth image into a pre-trained second body information model, to obtain height, weight, and posture information of the patient that is outputted by the second body information model, and provide the height, weight, and posture information of the patient to the medical imaging application apparatus, so that the medical imaging application apparatus uses the height, weight, and posture information to perform information registration for the patient.

The second body information model is obtained by training, using multiple sets of 2D color and depth images acquired in advance as an input parameter set, and using height, weight, and posture information, corresponding to each set of 2D color and depth images and acquired in advance, as an output parameter set.

Figure 6:
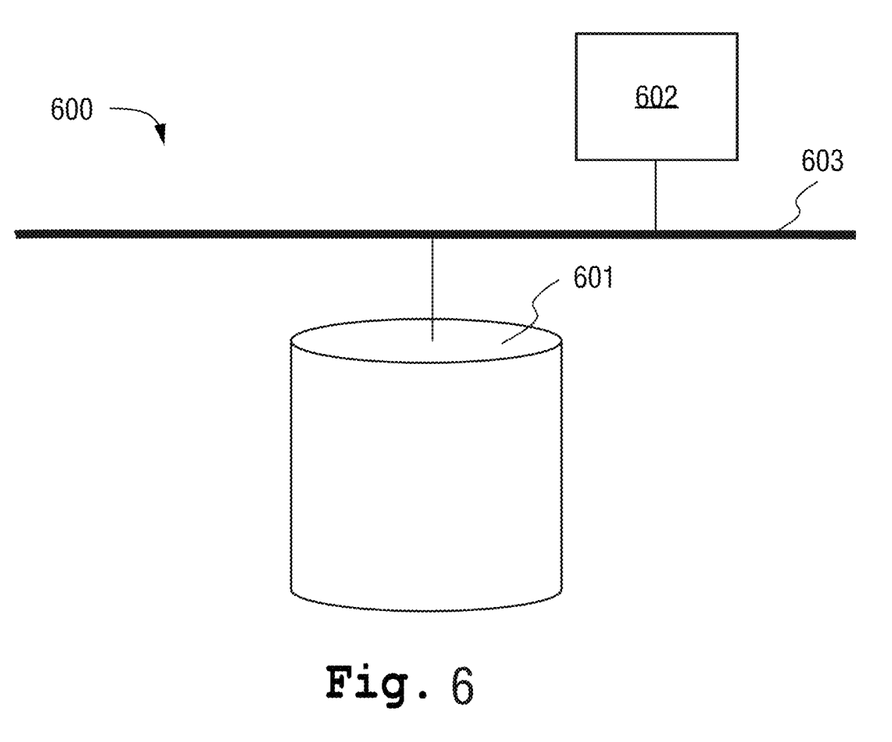
FIG. 6 is an example structural diagram of another acquisition control and image analysis apparatus in an embodiment of the present disclosure.

FIG. 6 is an example of a structural diagram of another acquisition control and image analysis apparatus in an embodiment of the present disclosure. As shown in FIG. 6, the apparatus 600 may comprise at least one memory 601 and at least one processor 602. In addition, some other components may also be included, such as a communication port, etc. These components communicate via a bus 603.

The at least one memory 601 is configured to store a computer program. In one embodiment, the computer program may be understood to comprise the modules of the acquisition control and image analysis apparatus 500 shown in FIG. 5. Furthermore, the at least one memory 601 may also store an operating system, etc. Operating systems include but are not limited to: an Android operating system, a Symbian operating system, a Windows operating system, a Linux operating system, etc.

The at least one processor 602 is configured to call (e.g. retrieve and/or execute instructions) of the computer program stored in the at least one memory 601, and to perform the method of FIG. 2 in an embodiment of the present disclosure. The processor 602 may be a CPU, a processing unit/module, an ASIC, a logic module or a programmable gate array, etc. The processor 602 can receive and send data via a communication port.

Figure 7:
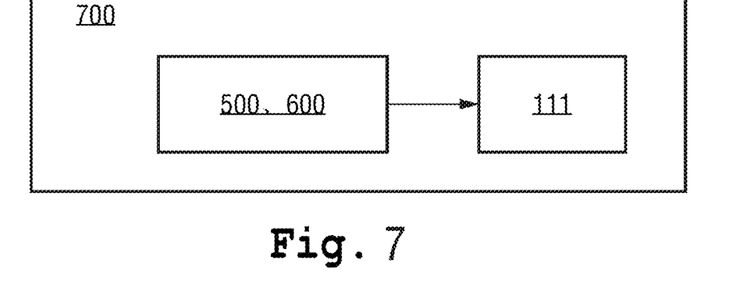
FIG. 7 is an example structural diagram of the image acquisition and analysis system in an embodiment of the present disclosure.

FIG. 7 is an example structural diagram of the image acquisition and analysis system in an embodiment of the present disclosure. As shown in FIG. 7, the system 700 may comprise the 3D camera 111 mounted at a set position above the medical imaging system and the acquisition control and image analysis apparatus 500 or 600 as described in either embodiment in FIG. 5 or FIG. 6.

Figure 8:
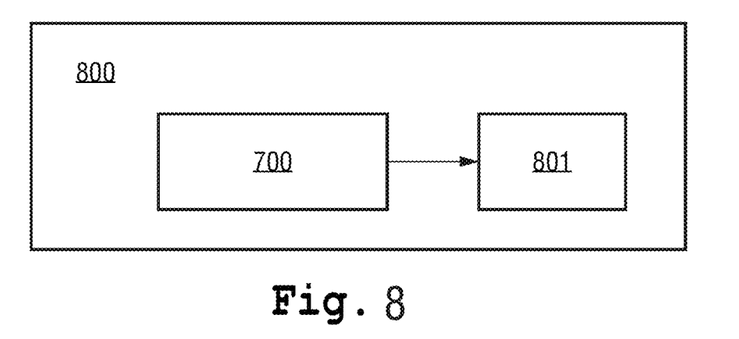
FIG. 8 is an example structural diagram of a system for scan preparation in a medical imaging system in an embodiment of the present disclosure.

FIG. 8 is an example structural diagram of a system for scan preparation in a medical imaging system in an embodiment of the present disclosure. As shown in FIG. 8, the system 800 may comprise the image acquisition and analysis system 700 of FIG. 7 and the medical imaging application apparatus 801.

The medical imaging application apparatus 801 is configured to determine position information of a current scanning region in the patient bed coordinate system according to the position information of multiple candidate scanning regions in the patient bed coordinate system that is provided by the image acquisition and analysis system 700, and control the patient bed to move the current scanning region to the scanning center of the medical imaging device according to the position information of the current scanning region in the patient bed coordinate system and the position of the patient bed relative to the scanning center; to perform information registration for the patient according to the height, weight, and posture information of the patient that is provided by the image acquisition and analysis system 700; and to determine candidate scanning regions supported by the medical imaging system according to any one of, or any combination of, information of the body region covered by the coil that is provided by the image acquisition and analysis system 700, the candidate scanning regions supported by the image acquisition and analysis system 700 and acquired in advance, and the scanning region supported by the coil that is determined in advance, and then select the current scanning region from the candidate scanning regions supported by the medical imaging system.

Not all of the steps and modules in the flows and structural diagrams described herein are necessary; certain steps or modules may be omitted according to actual requirements or the needs of the particular application or implementation. The order in which steps are executed is not fixed, but may be adjusted as required. The partitioning of the modules is merely functional partitioning, employed for the purpose of facilitating description; during actual implementation, one module may be realized by multiple modules, and the functions of multiple modules may be realized by the same module; these modules may be located in the same device or in different devices. For example, the acquisition control module 501 and image analysis module 502 in the acquisition control and image analysis apparatus may be located in the same computer, e.g. both be located in the abovementioned dedicated computer 112, in a computer where the medical imaging application apparatus is located, or may be located in different computers; for example, the acquisition control module 501 may be located in the dedicated computer 112 while the image analysis module 502 may be located in the computer where the medical imaging application apparatus is located.

Figure 9:
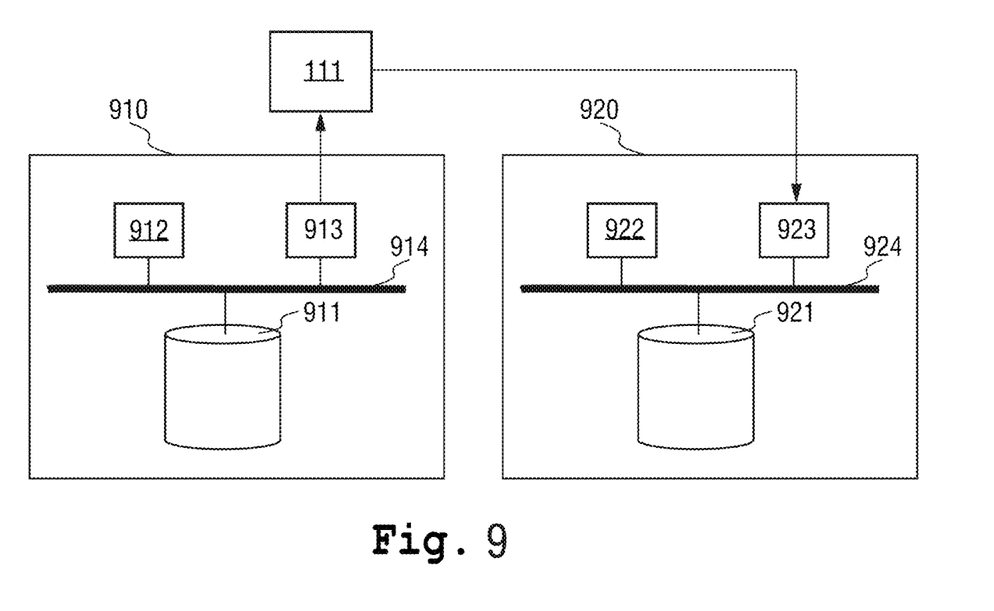
FIG. 9 is an example structural diagram of another system for scan preparation in a medical imaging system in an embodiment of the present disclosure.

For example, FIG. 9 shows an example structural diagram of another system for scan preparation in a medical imaging system in an embodiment of the present disclosure. As shown in FIG. 9, the following are included: a first apparatus 910 and a second apparatus 920. The first apparatus 910 comprises a first memory 911, a first processor 912, and a first communication port 913. In addition, some other components may also be included. These components communicate via a first bus 914.

The first memory 911 is configured to store a computer program. In one embodiment, the computer program may be understood to comprise the acquisition control module 501 shown in FIG. 5. Furthermore, the first memory 911 may also store an operating system, etc. Operating systems include but are not limited to: an Android operating system, a Symbian operating system, a Windows operating system, a Linux operating system, etc.

The first processor 912 is configured to call (retrieve and/or execute instructions) the computer program stored in the first memory 911 to perform corresponding operations of the acquisition control module 501. For example, this at least comprises: triggering, via the first communication port 913, the 3D camera mounted above the patient bed to acquire a 2D color and depth image of the patient at a present time, when the patient bed in the medical imaging system is at the predetermined position (e.g. an origin position or approximate origin position). When the patient bed in the medical imaging system is at the predetermined position, the 3D camera is told via the first communication port 913 to stop image acquisition. The first processor 912 may be a CPU, a processing unit/module, an ASIC, a logic module or a programmable gate array, etc.

The second apparatus 920 comprises a second memory 921, a second processor 922, and a second communication port 923. In addition, some other components may also be included. These components communicate via a second bus 924.

The second memory 921 is configured to store a computer program. In one embodiment, the computer program may be understood to include the image analysis module 502 shown in FIG. 5 and the medical imaging application apparatus 801 shown in FIG. 8. Furthermore, the second memory 921 may also store an operating system, etc. Operating systems include but are not limited to: an Android operating system, a Symbian operating system, a Windows operating system, a Linux operating system, etc.

The second processor 922 is configured to call (e.g. retrieve and/or execute instructions) for the computer program stored in the second memory 921, and to perform corresponding operations of the image analysis module 502 and the medical imaging application apparatus 801. For example, this at least includes the following operations:

receiving, via the second communication port 923, the 2D color and depth image acquired by the 3D camera, and inputting the 2D color and depth image into a pre-trained first body information model, to obtain position information, outputted by the first body information model, of multiple body feature site points in a camera coordinate system or patient bed coordinate system; wherein the first body information model is obtained by training, using multiple sets of 2D color and depth images acquired in advance as an input parameter set, and using position information of multiple body feature site points in the camera coordinate system or patient bed coordinate system, corresponding to each set of 2D color and depth images and acquired in advance, as an output parameter set;

when the position information is position information in the camera coordinate system, converting the position information of the multiple body feature site points in the camera coordinate system into position information in the patient bed coordinate system, according to a conversion relationship between the patient bed coordinate system and the camera coordinate system that is determined when the camera is calibrated;

calculating position information of multiple candidate scanning regions in the patient bed coordinate system, according to the position information of the multiple body feature site points in the patient bed coordinate system;

obtaining determined position information of a current scanning region in the patient bed coordinate system according to the position information of the multiple candidate scanning regions in the patient bed coordinate system, and controlling the patient bed to move the current scanning region to the scanning center of the medical imaging device according to the position information of the current scanning region in the patient bed coordinate system and the position of the patient bed relative to the scanning center.

In addition, when a coil covers a body region of the patient, it is possible to further obtain information of the body region covered by the coil that is outputted by the first body information model; and determine candidate scanning regions supported by the medical imaging system according to the information of the body region covered by the coil, and then select the current scanning region from the candidate scanning regions supported by the medical imaging system.

In other embodiments, the following operations are further included: inputting the 2D color and depth image into a pre-trained second body information model, to obtain height, weight, and posture information of the patient that is outputted by the second body information model; wherein the second body information model is obtained by training, using multiple sets of 2D color and depth images acquired in advance as an input parameter set, and using height, weight, and posture information, corresponding to each set of 2D color and depth images and acquired in advance, as an output parameter set;

performing information registration for the patient according to the height, weight, and posture information of the patient. This may specifically comprise: in a patient registration stage, the medical imaging application apparatus pre-filling a corresponding information box with the height, weight, and posture information for presentation to the user. Alternatively, it may comprise: upon receiving a scan initiation instruction triggered by the user, the medical imaging application apparatus comparing the height, weight, and posture information with height, weight, and posture information registered in advance by the user, and when deviation information of the height and weight exceeds a set threshold or the posture information is not consistent (e.g. exceeds a predetermined difference threshold or error), popping up a warning message box, and determining height, weight, and posture information to be used in the current scan according to a user selection.

It can be understood that hardware modules in the embodiments above may be realized mechanically or electronically. For example, one hardware module may comprise a specially-designed permanent circuit or logic device (such as a dedicated processor, such as an FPGA or ASIC) for completing a specific operation. The hardware module may also comprise a programmable logic device or circuit that is temporarily configured by software (e.g. comprising a general processor or another programmable processor) for executing a specific operation. The choice of whether to specifically use a mechanical method, a dedicated permanent circuit, or a temporarily configured circuit (e.g. configured by software) to realize the hardware module can be decided according to considerations of cost and time.

In addition, in an embodiment of the present disclosure, a computer readable storage medium is further provided (e.g. a non-transitory computer-readable medium), having stored thereon a computer program that can be executed by a processor to realize the method for scan preparation in a medical imaging system in embodiments of the present disclosure. Specifically, a system or apparatus equipped with a storage medium may be provided; software program code realizing the function of any one of the embodiments above is stored on the storage medium, and a computer (or CPU or MPU) of the system or apparatus is caused to read and execute the program code stored in the storage medium. Furthermore, it is also possible to cause an operating system etc. operating on a computer to complete a portion of, or all, actual operations by means of an instruction based on program code. It is also possible for program code read out from the storage medium to be written into a memory installed in an expansion board inserted in the computer, or written into a memory installed in an expansion unit connected to the computer, and thereafter instructions based on the program code cause a CPU etc. installed on the expansion board or expansion unit to execute a portion of and all actual operations, so as to realize the function of any one of the embodiments above. Embodiments of storage media used for providing program code include floppy disks, hard disks, magneto-optical disks, optical disks (such as CD-ROM, CD-R, CD-RW, DVD-ROM, DVD-RAM, DVD-RW, DVD+RW), magnetic tapes, non-volatile memory cards and ROM. Optionally, program code may be downloaded from a server computer via a communication network.

As can be seen from the solution above, in embodiments of the present disclosure, the 3D camera is used to acquire a 2D color and depth image of the patient at the present time, and the image acquired by the 3D camera is inputted into a pre-trained first body information model, and it is then possible to obtain position information, outputted by the first body information model, of body feature site points in the camera coordinate system or patient bed coordinate system, then position information of multiple candidate scanning regions in the patient bed coordinate system is calculated, this information is provided to the medical imaging application apparatus of the medical imaging system, the medical imaging application apparatus determines therefrom position information of a selected current scanning region in the patient bed coordinate system, and controls the patient bed to move the current scanning region to the scanning center of the medical imaging device according to the position information of the current scanning region in the patient bed coordinate system and the position of the patient bed relative to the scanning center, thereby realizing automation of patient positioning in the scan preparation process.

In addition, the image acquired by the 3D camera is further inputted into a pre-trained second body information model, and height, weight, and posture information of the patient that is outputted by the second body information model is obtained; the height, weight and posture information of the patient is provided to the medical imaging application apparatus, so that the medical imaging application apparatus uses the height, weight, and posture information to perform information registration for the patient, thereby realizing automation of patient registration in the scan preparation process.

Furthermore, the first body information model is trained to further output information of a body region covered by a coil, and the information of the body region covered by the coil is provided to the medical imaging application apparatus, so that the medical imaging application apparatus uses the information of the body region covered by the coil to determine or reduce the scope of scanning regions currently supported by the medical imaging system.

The embodiments above are merely preferred embodiments of the present disclosure, which are not intended to limit it. Any amendments, equivalent substitutions or improvements etc. made within the spirit and principles of the present disclosure shall be included in the scope of protection thereof.

What is claimed is:

1. A method for scan preparation in a medical imaging system, comprising:
   triggering, via one or more processors, a 3D camera mounted above a patient bed associated with the medical imaging system to acquire a 2D color and depth image of a patient when the patient bed is at a predetermined position;
   inputting, via one or more processors, the 2D color and depth image acquired by the 3D camera into a first body information model;
   receiving, via one or more processors, position information that is output by the first body information model of multiple body feature site points in accordance with one of a camera coordinate system or a patient bed coordinate system, wherein, when the position information is output in accordance with the camera coordinate system, converting, via one or more processors, the position information in accordance with the camera coordinate system into position information in accordance with the patient bed coordinate system using a conversion relationship between the patient bed coordinate system and the camera coordinate system that is determined from a calibration of the 3D camera;

calculating, via one or more processors, position information of multiple candidate scanning regions in accordance with the patient bed coordinate system using the position information of the multiple body feature site points;

providing, via one or more processors, the position information of the multiple candidate scanning regions to a medical imaging application apparatus;

upon receiving a scan initiation instruction triggered by a user, comparing a height, weight, and posture information of the patient with respective height, weight, and posture information registered in advance by the user; and when (i) a deviation of the height and weight exceeds a respectively set threshold, or (ii) the posture information differs from a predetermined difference threshold, presenting a warning message box and determining height, weight, and posture information to be used in the current scan according to a user selection, wherein the medical imaging application apparatus determines position information of a current scanning region in accordance with the patient bed coordinate system and controls the patient bed to move the current scanning region to a scanning center of a medical imaging device using the position information of the current scanning region and the position of the patient bed relative to the scanning center.

2. The method for scan preparation in a medical imaging system as claimed in claim 1, further comprising:

when a coil covers a body region of the patient, obtaining information of the body region covered by the coil that is output by the first body information model; and providing the information of the body region covered by the coil to the medical imaging application apparatus, wherein the medical imaging application apparatus determines one or more candidate scanning regions supported by the medical imaging system using the information of the body region covered by the coil and selects the current scanning region from among the one or more candidate scanning regions.

3. The method for scan preparation in a medical imaging system as claimed in claim 1, further comprising:

inputting the 2D color and depth image into a pre-trained second body information model, wherein the height, weight, and posture information of the patient is output by the second body information model, and wherein the second body information model is generated by (i) training, using multiple sets of 2D color and depth images acquired in advance as an input parameter set, and (ii) using height, weight, and posture information corresponding to each set of 2D color and depth images acquired in advance as an output parameter set; and providing the height, weight, and posture information of the patient to the medical imaging application apparatus, wherein the medical imaging application apparatus uses the height, weight, and posture information to perform information registration for the patient.

4. The method for scan preparation in a medical imaging system as claimed in claim 3, wherein medical imaging application apparatus using the height, weight, and posture information to perform the information registration for the patient comprises:

pre-filling a corresponding information box with the height, weight, and posture information for presentation to a user as part of a patient registration stage.

5. The method for scan preparation in a medical imaging system as claimed in claim 1, wherein the predetermined position of the patient bed is an origin position of the patient bed.

6. The method for scan preparation in a medical imaging system as claimed in claim 1, wherein the first body information model is generated by (i) training, using multiple sets of predetermined 2D color and depth images as an input parameter set, and (ii) using position information of multiple body feature site points in the camera coordinate system or the patient bed coordinate system corresponding to each set of the predetermined 2D color and depth images as an output parameter set.

7. An acquisition control and image analysis apparatus, comprising:

an acquisition control module configured to trigger a 3D camera mounted above a patient bed in a medical imaging system to acquire a 2D color and depth image of a patient when the patient bed is at a predetermined position; and an image analysis module configured to:

input the 2D color and depth image into a first body information model;

receive position information that is output by the first body information model of multiple body feature site points in accordance with one of a camera coordinate system or a patient bed coordinate system;

when the position information is output in accordance with the camera coordinate system, convert the position information in accordance with the camera coordinate system into position information in accordance with the patient bed coordinate system using a conversion relationship between the patient bed coordinate system and the camera coordinate system that is determined from a calibration of the 3D camera;

calculate position information of multiple candidate scanning regions in accordance with the patient bed coordinate system using the position information of the multiple body feature site points; and providing the position information of the multiple candidate scanning regions to a medical imaging application apparatus, wherein the medical imaging application apparatus is configured to:

upon receiving a scan initiation instruction triggered by a user, compare a height, weight, and posture information of the patient with respective height, weight, and posture information registered in advance by the user; and when (i) a deviation of the height and weight exceeds a respectively set threshold, or (ii) the posture information differs from a predetermined difference threshold, present a warning message box and determining height, weight, and posture information to be used in the current scan according to a user selection, and determine position information of a current scanning region in accordance with the patient bed coordinate system and moves the current scanning region to a scanning center of a medical imaging device using the position information of the current scanning region and the position of the patient bed relative to the scanning center.

8. The acquisition control and image analysis apparatus as claimed in claim 7, wherein the image analysis module is further configured to:
when a coil covers a body region of the patient, obtain information of the body region covered by the coil that is output by the first body information model; and
provide the information of the body region covered by the coil to the medical imaging application apparatus,
wherein the medical imaging application apparatus determines one or more candidate scanning regions supported by the medical imaging system using the information of the body region covered by the coil, and selects the current scanning region from among the one or more candidate scanning regions.

9. The acquisition control and image analysis apparatus as claimed in claim 7, wherein the image analysis module is further configured to:
input the 2D color and depth image into a trained second body information model; and
wherein the height, weight, and posture information of the patient is output by the second body information model,
wherein the second body information model is generated by (i) training, using multiple sets of predetermined 2D color and depth images as an input parameter set, and (ii) using height, weight, and posture information corresponding to each set of the predetermined 2D color and depth images as an output parameter set, and
provide the height, weight, and posture information of the patient to the medical imaging application apparatus,
wherein the medical imaging application apparatus uses the height, weight, and posture information to perform information registration for the patient.

10. The acquisition control and image analysis apparatus as claimed in claim 7, wherein the first body information model is generated by (i) training, using multiple sets of predetermined 2D color and depth images as an input parameter set, and (ii) using position information of multiple body feature site points in the camera coordinate system or the patient bed coordinate system corresponding to each set of the predetermined 2D color and depth images as an output parameter set.

11. The acquisition control and image analysis apparatus as claimed in claim 7, wherein the predetermined position of the patient bed is an origin position of the patient bed.

12. A system for scan preparation in a medical imaging system, comprising:
a first memory and a first processor, the first memory being configured to store a first computer program, and the first processor being configured to execute the first computer program to trigger a 3D camera mounted above a patient bed associated with the medical imaging system to acquire a 2D color and depth image of a patient when the patient bed is at a predetermined position; and
a second memory and a second processor, the second memory being configured to store a second computer program, and the second processor being configured to execute the second computer program to:
input the 2D color and depth image into a first body information model;
obtain position information that is output by the first body information model of multiple body feature site points in accordance with one of a camera coordinate system or patient bed coordinate system;
when the position information is accordance with the camera coordinate system, convert the position information in accordance with the camera coordinate system into position information in accordance with the patient bed coordinate system using a conversion relationship between the patient bed coordinate system and the camera coordinate system that is determined from a calibration of the 3D camera;
calculate position information of multiple candidate scanning regions using the position information of the multiple body feature site points;
obtain determined position information of a current scanning region using the position information of the multiple candidate scanning regions;
upon receiving a scan initiation instruction triggered by a user, compare a height, weight, and posture information of the patient with respective height, weight, and posture information registered in advance by the user;
when (i) a deviation of the height and weight exceeds a respectively set threshold, or (ii) the posture information differs from a predetermined difference threshold, present a warning message box and determining height, weight, and posture information to be used in the current scan according to a user selection,
and
control the patient bed to move the current scanning region to a scanning center of a medical imaging device associated with the medical imaging system according to the position information of the current scanning region and the position of the patient bed relative to the scanning center.

13. The system as claimed in claim 12, wherein the second processor is further configured to execute the second computer program to:
when a coil covers a body region of the patient, obtain information of the body region covered by the coil that is output by the first body information model; and
provide the information of the body region covered by the coil to the medical imaging system,
wherein the medical imaging system determines one or more candidate scanning regions supported by the medical imaging system using the information of the body region covered by the coil, and selects the current scanning region from among the one or more candidate scanning regions.

14. The system as claimed in claim 12, wherein the second processor is further configured to execute the second computer program to:
input the 2D color and depth image into a trained second body information model; and
wherein the height, weight, and posture information of the patient is output by the second body information model,
wherein the second body information model is generated by (i) training, using multiple sets of predetermined 2D color and depth images as an input parameter set, and (ii) using height, weight, and posture information corresponding to each set of the predetermined 2D color and depth images as an output parameter set, and
provide the height, weight, and posture information of the patient to the medical imaging system, wherein the medical imaging system uses the height, weight, and posture information to perform information registration for the patient.

15. The system as claimed in claim 12, wherein the second processor is further configured to execute the second computer program to generate the first body information model by (i) training, using multiple sets of predetermined 2D color and depth images as an input parameter set, and (ii) using position information of multiple body feature site points in the camera coordinate system or the patient bed coordinate system corresponding to each set of the predetermined 2D color and depth images as an output parameter set.

16. The system as claimed in claim 12, wherein the predetermined position of the patient bed is an origin position of the patient bed.

* * * * *